United States Patent [19]

DeLuca et al.

[11] 4,248,791

[45] Feb. 3, 1981

[54] 25-HYDROXY-26,26,26,27,27,27-HEXA-FLUOROCHOLECALCIFEROL

[75] Inventors: Hector F. DeLuca; Yoko Tanaka, both of Madison, Wis.; Nobuo Ikekawa, Musashinoshi; Yoshiro Kobayashi, Tokyo, both of Japan

[73] Assignee: Wisconsin Alumni Research Foundation, Madison, Wis.

[21] Appl. No.: 118,149

[22] Filed: Feb. 4, 1980

[51] Int. Cl.$^3$ .......................... C07J 9/00; A61K 31/59
[52] U.S. Cl. .................................................. 260/397.2
[58] Field of Search ...................................... 260/397.2

[56] References Cited

U.S. PATENT DOCUMENTS 4,069,321   1/1978   Jones et al. ...................... 260/397.2

Primary Examiner—Elbert L. Roberts
Attorney, Agent, or Firm—Howard W. Bremer

[57] ABSTRACT

The invention provides a new derivative of vitamin D, 25-hydroxy-26,26,26,27,27,27-hexafluorocholecalciferol and a process for preparing the same.

The compound is characterized by vitamin D-like activity in their ability to increase intestinal calcium transport, increase serum calcium and to prevent the development of rickets. These compounds would find ready application as a substitute for vitamin D and in the treatment of disease states evincing metabolic calcium and phosphorus deficiencies.

8 Claims, No Drawings

25-HYDROXY-26,26,26,27,27,27-HEXAFLUORO-CHOLECALCIFEROL

The invention described herein was made in the course of work under a grant or award from the Department of Health, Education, and Welfare, and U.S. Japan Cooperative Grant INT-76-05793 and IPA No. 0001 awarded by the National Science Foundation.

DESCRIPTION

Technical Field

This invention relates to a compound which is characterized by vitamin D-like activity.

More specifically this invention relates to a derivative of vitamin $D_3$.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective, vitamin $D_3$ must be converted in vivo to its hydroxylated forms. For example, the vitamin is first hydroxylated in the liver to form 25-hydroxy-vitamin $D_3$ and is further hydroxylated in the kidney to produce $1\alpha,25$-dihydroxy vitamin $D_3$ or 24,25-dihydroxy vitamin $D_3$. The $1\alpha$-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

Background Art

Since the discovery of biologically active metabolites of vitamin D there has been much interest in the preparation of structural analogs of these metabolites, because such compounds may represent useful therapeutic agents for the treatment of diseases resulting from calcium metabolism disorders. A variety of vitamin D-like compounds have been synthesized. See, for example, U.S. Pat. Nos. 3,741,996 directed to $1\alpha$-hydroxycholecalciferol; 3,907,843 directed to $1\alpha$-hydroxyergocalciferol; 3,786,062 directed to 22-dehydro-25-hydroxycholecalciferol; 3,906,014 directed to 3-deoxy-$1\alpha$-hydroxycholecalciferol; and 4,069,321 directed to the preparation of various side chain-fluorinated vitamin $D_3$ derivatives and side chain-fluorinated dihydrotachysterol analogs.

Disclosure of Invention

A new derivative of vitamin $D_3$ has been prepared which expresses excellent vitamin D-like activity as measured by its ability to stimulate clacium transport in intestine in its ability to mobilize calcium from bone (serum calcium level increase) and in its antirachitic activity as measured by the rat line test. Such compound, therefore, could serve as a substitute for vitamin D in its various known applications and would be useful in the treatment of various metabolic bone diseases.

This derivative has been identified as 25-hydroxy-26,26,26,27,27,27,-hexafluorocholecalciferol (25-hydroxy-26,26,26,27,27,27-hexafluorovitamin $D_3$ or 25-OH-26,27-$F_6$-$D_3$).

Best Mode for Carrying Out the Invention

The compound of this invention was synthesized in accordance with the following description and abbreviated schematic:

The starting material in the process, namely, $3\beta$-hydroxychol-5-en-24-ol tetrahydropyranyl ether (1) is readily available by treatment of commercially available cholenic acid or cholenic acid esters. For example, by converting the cholenic acid or cholenic acid ester to the 3-tetrahydropyranyl derivative followed by reduction of the acid or ester function with a metal hydride such as lithium aluminum hydride, all of which procedures are well known.

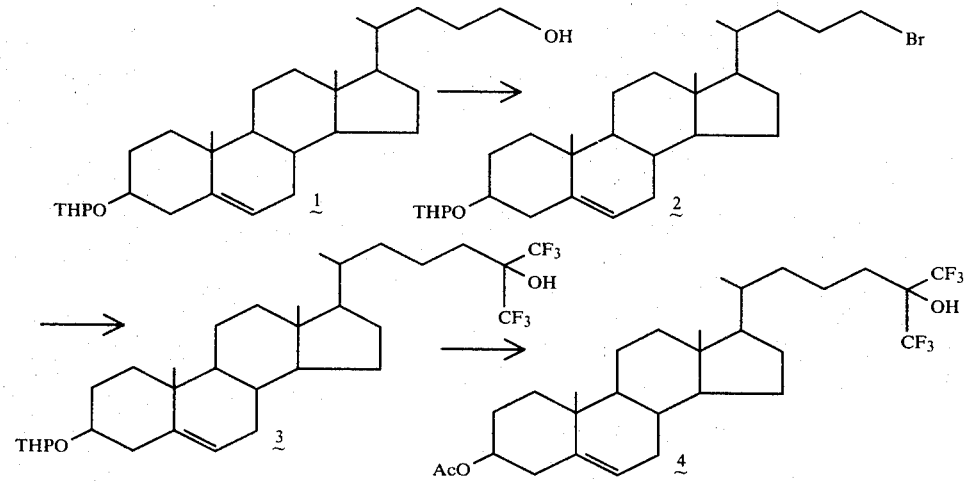

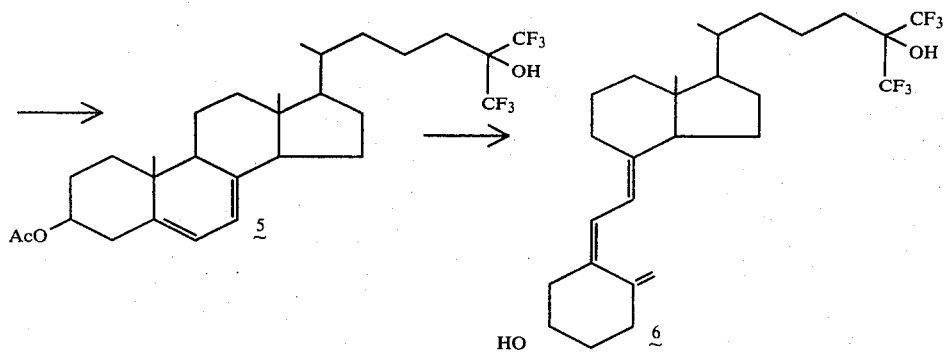

Synthesis of 25-hydroxy-26,26,26,27,27,27-Hexafluorovitamin D₃

3β-Hydroxychol-5-enyl bromide tetrahydropyranyl ether (2)

To a solution of 3β-hydroxychol-5-en-24-ol tetrahydropyranyl ether (1) (1.4 g, 3.15 mmol) in tetrahydrofuran (THF) (15 ml) was added a hexane solution of n-butyl lithium (3.5 mmol) at −78°. After stirring for 5 min, p-toluenesulfonyl chloride (670 mg, 3.5 mmol) in THF (5 ml) was added and the mixture was stirred for 1 hr. The reaction mixture was poured onto ice-water and extracted with methylene chloride. After washing with water and drying over MgSO₄, the solvent was removed by evaporation. The residue was dissolved in a mixture of THF (15 ml) and acetone (15 ml), and was then added to lithium bromide (3.0 g). After refluxing for 2 hr, the precipitate was removed by filtration and the filtrate was chromatographed on silica gel column. Elution with methylene chloride gave 2 (1.414 g, 88%), mp 117-119° (from methanol-acetone); Anal. Calcd. for C₂₉H₄₇O₂Br; C, 68.62; H, 9.33. Found: C, 68.84; H, 9.43.

3β-Acetoxy-26,26,26,27,27,27-hexafluoro-25-hydroxy-cholest-5-ene (4)

A suspension of potassium (150mg) and magnesium chloride (200 mg) in THF (5 ml) was refluxed for 2 hr under argon, and then cooled to room temperature. The bromide 2 (254 mg, 0.5 mmol) in THF (5 ml) was added and the mixture was stirred for 2 hr at room temperature. Under cooling with dry-ice/acetone, an excess of hexafluoroacetone gas was introduced and the mixture was stirred for 15 min; methanol (5 ml) was added and the mixture stirred for 10 min at room temperature. After addition of dilute HCl, the reaction mixture was extracted with ether. The extract was chromatographed on a silica gel column. From the eluate with benzene-ether (30:1), the hexafluoride 3 (48mg, 16%) was obtained, MS, m/e 510

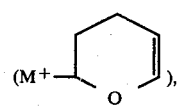

492, 477, 255; NMR (CDCl₃), δ, 0.68 (s, C-18), 0.94 (d, J=6 Hz, C-21), 1.00 (s, C-19), 3.88 (m, C-3), 3.48

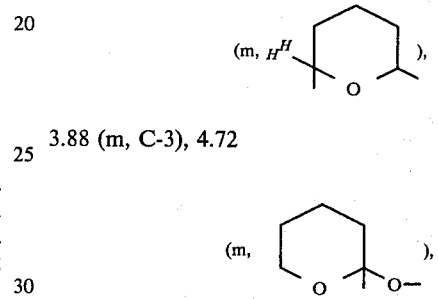

5.32 (m, C-6).

The hexafluoride 3 was dissolved in methanol (3 ml) and methylene chloride (3 ml), and was added with p-toluenesulfonic acid (10 mg) giving the corresponding 3-hydroxy compound. The mixture was stirred for 2 hr at room temperature, and then concentrated under vacuo. The residue was dissolved in methylene chloride (2 ml), stirred with acetic anhydride (1 ml) and pyridine (1 ml) for 16 hr. The product was purified with a silica gel column to give 28 mg of the 3-acetate 4, mp 165°-166°; MS, m/e 492 (M⁺-AcOH), 477, 384, 371, 255; NMR (CDCl₃), β, 0.68 (s, C-18), 0.93 (d, j=6 Hz, C-21), 1.01 (s, C-19), 2.02 (s, Acetyl), 4.56 (m, C-3), 5.34 (m, C-6).

If desired, O-acyl protecting groups other than the 3-acetyl group can be utilized. For example, the tetrahydropyranyl group can be utilized, or an acyl moiety having from 1 to about 4 carbon atoms, e.g. acetyl, propionyl, butyryl, or an aromatic acyl, such as benzoyl or substituted benzoyl (nitro-benzoyl, chloro-benzoyl) can be used and readily obtained by reacting the 3-hydroxy compound with the appropriate anhydride or acyl halide, e.g. the chloride as is well known in the art. Thus, the substitutent at the 3-position in compounds 4 and 5 can be depicted as an RO-group where R is hydrogen, tetrahydropyranyl, an acyl group having from 1 to about 4 carbon atoms, benzoyl or substituted benzoyl.

3β-Acetoxy-26,26,26,27,27,27-hexafluorocholesta-5,7-dien-25-ol (5)

To a refluxing solution of the acetate 4 (19 mg) in CCl₄ (2 ml), N-bromosuccinimide (9 mg) was added and the mixture was refluxed for 20 min under argon. After cooling, the resulting precipitate was filtered off, and the filtrate was evaporated under vacuo. The residue was dissolved in xylene (1.5 ml) and dropped into a refluxing solution of s-collidine (0.5 ml) in xylene (1.5 ml). After refluxing for 10 min, the mixture was extracted with ethyl acetate. The crude product was dissolved in acetone (5 ml) and treated with p-toluenesulfonic acid (10 mg) by stirring for 14 hr at room temperature. After addition of water, the mixture was extracted with ethyl acetate. The reaction product was purified with preparative TLC (benzene-ethyl acetate, 50:1; two times) to give the 5,7-diene 5 (4.9 mg); UV, $\lambda_{Max}$(EtOH)262(sh), 271, 282, 293 nm.

25-Hydroxy-26,26,26,27,27,27-Hexafluorovitamin $D_3(\underline{6})$

The 5,7-diene 5 was irradiated in ehtanol (40 ml)-benzene (90 ml) solution with a medium pressure mercury lamp through a Vycor filter for 2.5 min under argon with ice-cooling. The reaction mixture was then refluxed for 1 hr. The solvent was evaporated and the residue was chromatographed on a silica gel column and then on preparative TLC (benzene-ethyl acetate, 50:1, two times) to give 1.2 mg of the crude vitamin D acetate. The solution of the acetate in THF (4 ml) was treated with 5% KOH in methanol (5 ml) for 13 hr at room temperature under argon. The product was extracted with ethyl acetate, and was purified with HPLC using a Zorbax-SIL column (15 cm X 4.6 mm i.d.) and a solvent of methylene chloride-hexane (2:1) to give 0.75 mg of 6; UV, $\lambda_{min}$(EtOH)227.5, $\lambda_{max}$264 nm; MS, m/e 508 (M+), 493, 490, 475, 271, 253, 136, 118.

The 25-OH-26,27-$F_6$-$D_3$ product can, if desired, be obtained in crystalline form by dissolution in a suitable solvent or solvent systems, e.g. ether, ether-hexane, methanol-ether, ethylacetatealkane, and then removing the solvents(s) by evaporation or other means as is well known.

Also, if desired, in the foregoing procedure the -5,7-diene (5) can be hydrolyzed in accordance with the foregoing procedure or other mild basic hydrolytic procedures well known in the art prior to irradiation to convert the acetoxy substituent at the 3-position to hydroxyl.

Biological Activity

The biological potency of 25-OH-26,27-$F_6$-$D_3$ is confirmed by appropriate in vivo assays in the rat. Male weanling rats were purchased from Holtzman Co. Wis. and fed ad libtum water and either one of a low-calcium-adequate phosphorus, vitamin D deficient diet as described by Suda et al (J. Nutrition 100, 1049, 1970) or high calcium-low phosphorus, vitamin D deficient diet as described by Tanaka and DeLuca (PNAS 71, 1040, 1974) for 3 weeks.

Intestinal calcium transport

Rats that had been fed the low calcium, vitamin D deficient diet for 3 weeks were divided into 3 groups of five rats each and were given respectively 650 pmole of either 25-OH-26,27-$F_6$-$D_3$ or 25-hydroxy $D_3$ (25-OHD$_3$) dissolved in 0.1 ml of 95% ethanol intrajugularly 22 hrs prior to sacrifice. The rats in the control group were given the ethanol vehicle in the same manner. They were killed by decapitation and the blood was collected. Their duodena were then immediately removed to measure the intestinal calcium transport activity by the method described by Martin and DeLuca (Am. J. Physiology 216, 1351, 1969). Results are shown in Table 1, first column.

Serum calcium concentration

The blood collected from rats as indicated above was centrifuged to obtain serum. 0.1 ml of serum was mixed with 1.9 ml of 0.1% lanthanum chloride solution and the calcium concentration was measured with an atomic absorption spectrophotometer (Perkin-Elmer Model HO-214). Results are shown in Table 1, second column.

Because of significantly greater ability of the 25-OH-26,27-$F_6D_3$ to increase serum calcium concentration in comparison with that of 25-OHD$_3$ as shown in Table 1, a time course study of increase of serum calcium in response to the administration of 25-OHD$_3$ or 25-OH-26,27-$F_6D_3$ was made.

Rats fed the low calcium vitamin D deficient diet for 3 weeks were divided into groups of 5 rats. The rats were given 325 pmole of either 25-OH-26,27-$F_6$-$D_3$ or 25-OHD$_3$ dissolved in 0.1 ml of 95% ethanol intrajugularly. The materials were administered either 6,17,27 or 48 hrs. prior to sacrifice.

Table 1

Intestinal calcium transport and increase in serum calcium concentration in response to a single dose of 25-OH-26,27-$F_6$-$D_3$ or 25-OHD$_3$.
(650 pmole)

| Compound Given | Intestinal Ca Transport $^{45}$Ca Inside $^{45}$Ca 0.60*(mg/100 ml) | Serum Calcium |
|---|---|---|
| Control | 2.1 ± 0.60 (a) | 3.6 ± 0.1(d) |
| 25-OH-26,27-$F_6$-$D_3$ | 5.6 ± 0.8(b) | 5.4 ± 0.1(e) |
| 25-OHD$_3$ | 4.9 ± 0.8(c) | 4.9 ± 0.3(f) |

*standard deviation of the mean
(b) and (c) from (a) p<0.001
(b) from (c) N.S.
(e) and (f) from (d) p<0.001
(e) from (f) p<0.005

Rats in the control group received the ethanol vehicle alone in the same manner. The rats were killed by decapitation at the indicated times, the blood was collected and centrifuged to obtain the serum. The serum calcium concentration was determined as indicated above. Results are shown in the following table.

TAble 2

| Compound | Serum Calcium Level in mg/100 ml Hours After Dose | | | |
|---|---|---|---|---|
| | 6 | 17 | 27 | 48 |
| Control | 4.1 | 4.3 | 4.1 | 4.0 |
| 25-OH-$D_3$ | 4.4 | 5.8 | 5.3(b) | 5.3 |
| 25-OH-26,27-$F_6$-$D_3$ | 4.7 | 5.7 | 6.2(a) | 1.8 |

(a) from (b) p<0.001

It is evident that not only does the hexafluoro compound of this invention induce a rapid increase in serum calcium (substantially equivalent to that induced by 25-OH-$D_3$) but that it maintains the serum calcium at a higher level than does 25-OH-$D_3$ over the remainder of the time course run.

Antirachitic activity

Rats fed the low phosphorus, vitamin D deficient diet as described above were divided into 3 groups of 5 rats. A Single dose of 325 pmole of either 25-OH-26,27-$F_6$-$D_3$ or 25-OHD$_3$ dissolved in 0.1 ml 95% ethanol was given intrajugularly one week prior to sacrifice. Rats in the control group received ethanol vehicle in the same manner. A week later, the rats were killed by decapitation and their duodena were used for measurment of intestinal calcium transport activity as described above.

Results are shown in Table 3, first column. Their radii and ulnae were removed and evaluated in accordance with the rat line test (U.S. Pharmacopoeia, 15th Ev., Mack Publishing Co., Easton, Pa. 1955, p. 889). Results obtained are shown in Table 3, second column.

Table 3

Intestinal calcium transport and antirachitic activity in response to a single dose (385 pmol) of 25-OH-26,27-$F_6$-$D_3$ or 25-OH$D_3$ given one week prior to sacrifice.

| Compound Given | Intestinal Ca Transport $^{45}$Ca Inside/$^{45}$Ca Outside | Antirachitic Activity (Unit) |
|---|---|---|
| Control | 2.0 ± 0.3*[a] | 0 |
| 25-OH-26,27-$F_6$-$D_3$ | 7.1 ± 1.4[b] | ≧6 |
| 25-OH$D_3$ | 6.9 ± 0.6[c] | ≧6 |

*standard derivation of the mean
[b] and [c] from [a]p<0.001
[b] from [c]N.S.

It is evident from the foregoing data that 25-OH-26,27-$F_6$-$D_3$ exhibits pronounced vitamin D-like activity and appears to be wholly as effective in this regard as 25-OH$D_3$.

The 25-OH-26,27-$F_6$-$D_3$ of this invention may be readily administered in sterile parenteral solutions by injection or intravenously or by alimentary canal in the form of oral dosages, or by suppository. Doses of from about 0.1 μg to about 2.5 μg per day are effective in obtaining the physiological calcium balance responses described and which are characteristic of vitamin D-like activity, with maintenance doses of about 0.25 μg being suitable.

Dosage form of the compound can be prepared by combining them with a non-toxic pharmaceuticully acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspension, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given the particular dose to be administered to a host will depend upon the specific disease state being treated, the end results being sought in a particular case, as well as other factors known to those skilled in the art in the therapeutic use of such medicinal agents.

We claim:

1. 25-hydroxy-26,26,26,27,27,27-hexafluoro cholecalciferol.
2. The compound of claim 1 in crystalline form.
3. Compounds having the formula

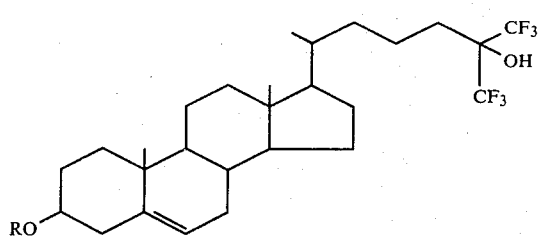

where R is selcted from the group consisting of hydrogen, tetrahydropyranyl, an alkyl group having from 1 to about 4 carbon atoms, benzoyl or substituted benzoyl.

4. 3β-acetoxy-26,26,26,27,27,27-hexafluorocholesta-5,7-dien-25-ol.
5. 3β-hydroxy-26,26,26,27,27,27-hexafluorocholesta-5,7-dien-25-ol.
6. Compounds having the formula

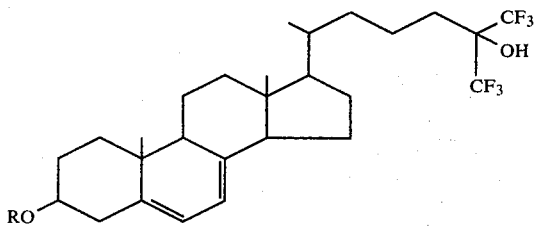

where R is selected from the group consisting of hydrogen, tetrahydropyranyl, an alkyl group having from 1 to about 4 carbon atoms, benzoyl or substituted benzoyl.

7. 3β-acetoxy-26,26,26,27,27,27-hexafluoro-25-hydroxycholest-5-ene.
8. 3β-hydroxy-26,26,26,27,27,27-hexafluoro-25-hydroxycholest-5-ene.

* * * * *

UNITED STATES PATENT OFFICE
CERTIFICATE OF CORRECTION

Patent No. 4,248,791  Dated February 3, 1981

Inventor(s) Hector F. DeLuca et al

It is certified that error appears in the above-identified patent and that said Letters Patent are hereby corrected as shown below:

In column 4, line 43, "$\beta$" should be --$\delta$--.

In column 6, line 49, "t. 8" should be -- 5.8 --.

In column 7, lines 13 and 14, "$\geqq 6$" should be --$\geq 6$--.

Signed and Sealed this

Nineteenth Day of May 1981

[SEAL]

*Attest:*

RENE D. TEGTMEYER

*Attesting Officer*  *Acting Commissioner of Patents and Trademarks*